United States Patent [19]

Golovin

[11] Patent Number: 5,489,491
[45] Date of Patent: Feb. 6, 1996

[54] CURABLE POLYMER PRECURSORS FOR SOLID ELECTROLYTES

[76] Inventor: Milton N. Golovin, 8 Wensley Dale Ct., Owings Mills, Md. 21117

[21] Appl. No.: 230,569

[22] Filed: Apr. 20, 1994

Related U.S. Application Data

[63] Continuation-in-part of Ser. No. 918,438, Jul. 22, 1992, Pat. No. 5,262,253, and a continuation-in-part of Ser. No. 168,881, Dec. 15, 1993, abandoned.

[51] Int. Cl.$^6$ ................................................ H01M 10/40
[52] U.S. Cl. .................... 429/192; 558/50; 558/55
[58] Field of Search ............................ 429/192; 558/45, 558/50, 55

[56] References Cited

U.S. PATENT DOCUMENTS

| 3,335,163 | 8/1967 | Tesoro et al. | 558/51 X |
| 4,079,084 | 3/1978 | Houghton | 558/46 X |
| 4,357,401 | 11/1982 | Andre et al. | 429/192 |
| 4,737,422 | 4/1988 | Knight et al. | 429/192 |
| 4,830,939 | 5/1989 | Lee et al. | 429/192 |
| 4,908,283 | 3/1990 | Takahashi et al. | 429/192 |
| 4,925,751 | 5/1990 | Shackle et al. | 429/192 X |
| 5,185,368 | 2/1993 | Peter et al. | 558/50 |
| 5,262,253 | 11/1993 | Golovin | 429/192 |

OTHER PUBLICATIONS

Fiona M. Gray, "Solid Polymer Electrolytes" VCH Publishers, Inc., New York, 1991, pp. 95–123 (month n/a).

*Primary Examiner*—Stephen Kalafut

[57] ABSTRACT

Vinyl sulfonate-derivatized oligomers of poly(oxyalkylene)glycols or polyesters and isocyanate are urethane linked polymer precursors for the solid polymeric matrix of a solid electrolyte. The solid polymeric matrix is made by crosslinking the vinyl sulfonate-derivatized oligomer.

11 Claims, No Drawings

CURABLE POLYMER PRECURSORS FOR SOLID ELECTROLYTES

This application is a continuation-in-part of U.S. application Ser. No. 07/918,438, filed Jul. 22, 1992, now U.S. Pat. No. 5,262,253 and U.S. application Ser. No. 08/168,881 NOVEL POLYMER PRECURSORS FOR SOLID ELECTROLYTES, filed Dec. 15, 1993, now abandoned.

FIELD OF THE INVENTION

The invention relates to polymers for solid polymeric electrolytes and their use in solid electrochemical cells. The invention particularly relates to polymer precursors for single-phase solid polymeric electrolytes.

BACKGROUND OF THE INVENTION

Solid electrolytes have been shown to have many advantages in the fabrication of electrochemical cells and batteries, such as thermostability, reduced corrosion of the electrodes, and cyclability. Furthermore, solid electrolytes permit us to create electrochemical sources of high energy per unit weight. Solid electrolytes, particularly polymeric electrolytes, have the principal advantage of being prepared in thin layers which reduces cell resistance and allows large drains at low current densities.

In the design of solid polymeric electrolytes both the properties of ionic conductivity and mechanical strength must be provided. It has been found advantageous to incorporate inorganic ion salts and solvents into the solid electrolytes, as well as to select polymers which enhance ionic conductivity. Cross-linking of the polymers can lead to stronger solid electrolytes, i.e. resilient thin layers of electrolyte, but cross-linking must not be to the detriment of ionic conductivity. Thermal and radiation-induced cross-linking (curing) have been extensively used for this purpose. Prior to crosslinking, the polymer or oligomer is termed a prepolymer or polymer precursor. U.S. Pat. No. 4,654,279 describes a two-phase solid polymeric electrolyte consisting of an interpenetrating network of a mechanically supporting phase consisting of cross-linked polymers, and a separate ionic conducting phase consisting of a metal salt and a complexing liquid therefore, which is a poly(alkylene oxide).

Poly (alkylene oxide), optionally derivatized with acryloyl and urethane groups is a polymer precursor for single-phase polymeric electrolytes. U.S. Pat. No. 4,908,283 discloses an acryloyl-derivatized solid polymeric electrolyte. However, radiation-cured solid polymeric electrolytes may lack sufficient mechanical strength and toughness. It is believed that the physical robustness of the cross-linked polymer is diminished by the presence of high molecular weight poly(oxyalkylene) units in the polymer precursors. Such poly(oxyalkylene) units are referred to as the "soft sectors" of the cross-linked polymer precursors because of this physical property. The art is seeking means for strengthening the poly(oxyalkylene) portions of the polymer precursor.

The chemical cross-linking of poly(alkylene oxide), for example, as disclosed in U.S. Pat. No. 3,734,876, was suggested as an alternative to radiation-induced cross-linking in order to obtain more control over the product's properties and synthesis.

The use of di-, tri- and polyisocyanates to create urethane linking groups between poly(oxyethylene) units for use as solid polymeric electrolytes is reported in U.S. Pat. No. 4,357,401. However, Fiona M. Gray, "Solid Polymer Electrolytes", VCH Publishers, Inc., New York, 1991, at page 103, reports that the incorporation of isocyanate units into the network polymer results in a polymeric electrolyte containing large quantities of bulky groups which are superfluous to the conduction mechanism and hinder ionic motion. In addition, it is reported that the urethane linkage has a strong influence in the glass transition temperature because of interactions between the urethane linkage and the poly(oxyalkylene) units.

It would be advantageous if thermal and radiation-curable polymer precursors based on urethane linked poly(oxyalkylene)glycols could be designed to lend mechanical strength to the solid polymeric electrolyte without loss of ionic conductivity.

SUMMARY OF THE INVENTION

The strengthening of the so-called poly(oxyalkylene) "soft sectors" in solid electrolyte polymers is accomplished by linking blocks of poly(oxyalkylene) units, —(CH$_2$CHR$^1$O)$_n$—, and/or polyester units, —(R$^2$OC(O)R$^3$C(O)O)$_m$—, with urethane linking groups, and terminating the chain with a vinyl sulfonate group before curing.

In another aspect of the present invention, the solid electrolyte polymer precursor is a vinyl sulfonate-derivatized compound which is also composed of blocks of poly(oxyalkylene) units, —(CH$_2$CHR$^1$O)$_n$—, and/or blocks of polyester units, —(R$^2$OC(O)R$^3$C(O)O)$_m$, linked by urethane units, —C(O)NHR$^4$NHC(O)O—, wherein n and m are integers from 1 to about 50; R$^1$ is H or C$_1$–C$_3$ alkyl, R$^2$ is a C$_1$–C$_{12}$ hydrocarbylene or oxyhydrocarbylene group; and R$^3$ and R$^4$ are independently C$_1$–C$_{12}$ hydrocarbylene groups.

In the present invention, while n and m may vary from about 2 to about 50 in each polyester or poly(oxyalkylene) unit, because several such units are linked by urethane linkages, the preferred value of n and m is an integer in the range of from about 2 to about 10, more preferably from about 2 to about 5.

In a particular embodiment, the invention is directed to a compound, finding use as a solid electrolyte polymer precursor, which is represented by Formula I:

$$V_k\text{—}Y\text{—}R_{2-k} \qquad \qquad \text{I}$$

wherein V represents the vinyl sulfonate moiety of Formula II and Y represents the repeating urethane-linked poly(oxyalkylene) and/or polyester units of Formula III, and R is hydrogen or C$_1$–C$_6$ alkyl:

$$CH_2\!=\!CH(R^5)S(O_2) \qquad \qquad \text{II}$$

$$\text{—O}(Z_nD)_qZ_n\text{—} \qquad \qquad \text{III}$$

wherein $Z_n$ represents the poly(oxyalkylene) unit —(CH$_2$CHR$^1$O)$_n$— or the polyester unit —(R$^2$OC(O)R$^3$C(O)O)$_n$—;

wherein D represents the urethane linkage —C(O)NHR$^4$NHC(O)O—;

wherein said Formula I, k is 1 or 2;

n is an integer from 1 to about 50; preferably from 2 to about 10; more preferably from 2 to about 5;

q is an integer from 1 to about 100;

R$^1$ is H, or C$_1$–C$_3$ alkyl;

$R^2$ is $C_1$–$C_{12}$ hydrocarbylene or oxyhydrocarbylene;

$R^3$ and $R^4$ are $C_1$–$C_{12}$ hydrocarbylene; and $R^5$ is H or a hydrocarbyl group of from 1 to 20 carbon atoms, preferably from 1 to about 7 carbon atoms.

Preferably Z is a (oxyalkylene) unit, more preferably (oxyethylene), —($CH_2CH_2O$)—, $Z_n$ represents a block of poly(oxyalkylene) units, —($CH_2CHR^1O)_n$—; $Z_n$ also represents a block of polyester units —($R^2OC(O)R^3C(O)O)_n$—, wherein $R^2$ and $R^3$ are hydrocarbylene groups derived from suitable diols and dicarboxylic acids respectively. For example, $R^2$ is —$CH_2CH_2$— (ethylene glycol); —($CH_2CH_2OCH_2CH_2$)— (diethylene oxide glycol); —($CH_2)_4$— (butylene glycol) and so forth. Similarly, $R^3$ is the hydrocarbylene portion of a suitable dibasic acid, such as glycolic acid, terephthalic acid and the like.

The urethane linking group denoted by D in Formula III is derived from a diisocyanate, and preferably $R^4$ is phenylene, $C_1$–$C_6$ alkyl-substituted phenylene, $C_2$–$C_6$ alkylene, $C_{13}$–$C_{16}$ diphenylalkane, and the like, as derived, for example, from hexamethylene diisocyanate, isophorone diisocyanate, xylene diisocyanate, and alkyl-substituted xylene diisocyanate; or $R^4$ may be derived from triisocyanates such as biuret and isocyanurate.

Preferably, the number average molecular weight of the polymer precursor is in the range of from about 200 to about 100,000, and more preferably is in the range of from about 1,000 to about 20,000, and most preferably from about 4,000 to about 15,000.

Another aspect of the invention is a solid electrolyte comprising a solid polymer matrix, solvent and an inorganic ion salt, wherein said polymer matrix is obtained by curing a polymer precursor represented by Formula I. Preferably actinic radiation is used to cure the polymer precursor.

Another aspect of this invention is an electrochemical cell which comprises: an anode comprising a compatible anodic material; a cathode comprising a compatible cathodic material; and interposed therebetween, a solid electrolyte which comprises: a solid polymeric matrix; an inorganic ion salt; and a solvent; wherein said polymeric matrix is obtained by polymerizing a polymer precursor represented by Formula I.

In yet another aspect of the invention, an electrochemical battery comprises at least two and preferably a plurality of electrochemical cells as heretofore described.

Yet another aspect of the invention is a method of making a solid electrolyte which comprises the steps of forming a mixture comprising a solvent, an inorganic ion salt and a polymer precursor represented by Formula I; and exposing said mixture to actinic radiation.

DETAILED DESCRIPTION OF PREFERRED EMBODIMENTS

As noted above, this invention is directed to solid, single phase, solvent-containing polymeric electrolytes, and in particular, to polymer precursors which are employed to make the ion-conducting polymeric electrolyte. However, prior to describing this invention in further detail, the following terms will first be defined.

Definitions

As used herein, the following terms have the following meanings.

The terms "solid, single phase polymeric electrolyte" and "solid polymeric electrolyte" refer to an ionically conducting polymeric solid, normally comprising an inorganic ion salt, a compatible electrolyte solvent, and a solid polymeric matrix.

The term "polymer precursor" refers to a pre-polymer, which is itself of substantial molecular weight greater than 300 and preferably greater than 500, and which undergoes crosslinking reactions when "cured". The polymer precursor contains at least one hetero atom capable of forming donor-acceptor bonds with inorganic cations, for example, oxygen, sulfur or nitrogen with alkali metal cations.

Within the scope of the present invention, the polymer precursor is an vinyl sulfonate-derivatized, urethane oligomer of poly(oxyalkylene) glycol and/or polyester and diisocyanate.

The term "macroglycol" refers to particular high molecular weight urethane oligomer with hydroxyl end groups i.e., H—Y—H (See Formula III). The macroglycol consists of poly(oxyalkylene) units and/or polyester units linked together by urethane groups, D, as previously defined. The molecular weight of the macroglycol is increased by increasing the number of polyester and/or poly(oxyalkylene) units so linked by reacting the terminal hydroxy groups with a diisocyanate, or triisocyanate, to produce urethane linkages. The macroglycol so-produced is reacted with vinyl sulfonyl chloride to provide the compound of Formula I. The number average molecular weight of the macroglycol ranges from about 200 to about 100,000, preferably from about 1,000 to about 50,000, more preferably from about 4,000 to about 15,000.

The term "salt" refers to any salt, for example, an inorganic salt, which is suitable for use in a solid electrolyte. Representative examples of suitable inorganic ion salts are alkali metal salts of less mobile artions of weak bases having a large artionic radius. Examples of such artions are $I^-$, $Br^-$, $SCN^-$, $ClO_4^-$, $BF_4^-$, $PF_6^-$, $AsF_6^-$, $CF_3COO^-$, $CF_3SO_3^-$ and the like. Specific examples of suitable inorganic ion salts include $LiClO_4$, $LiI$ $LiSCN$, $LiBF_4$, $LiAsF_6$, $LiCF_3SO_3$, $LiN(CF_3SO_3)_2$, $LiPF_6$, $NaSCN$, $KI$, and the like. The inorganic ion salt preferably contains at least one atom selected from the group consisting of Li, Na and K.

The term "solid polymeric matrix" refers to an ionically conducting matrix formed by polymerizing an organic prepolymer, i.e. a polymer precursor containing at least one hetero atom capable of forming donor-acceptor bonds with inorganic cations derived from inorganic ion salts under conditions such that the resulting polymer is useful in preparing solid polymeric electrolytes. Solid polymeric matrices are well known in the art and are described for example in U.S. Pat. Nos. 4,908,283 and 4,925,751, both of which are incorporated herein by reference in their entirety.

The solid polymeric matrix of the present invention is derived from the polymer precursor of the present invention by cross linking (curing) the components of the polymer precursor. Such cross linking or curing is achieved chemically and is induced by thermal means or actinic radiation, preferably by actinic radiation. "Actinic radiation" refers to any radiation or particulate beam having the ability to induce the desired chemical reaction. Consequently, the actinic radiation is of an energy content which is appropriate to the desired reaction. In the practice of the present invention, the use of electron beam generators and ultraviolet light sources, well known to the art, produce actinic radiation of appropriate energy to cure an electrolyte mixture comprising a solid electrolyte polymer precursor.

The term "compatible electrolyte solvent", or in the context of components of the solid electrolyte, just "solvent", is a low molecular weight plasticizer added to the electrolyte and/or the cathode composition in which may also serve the purpose of solubilizing the inorganic ion salt. The solvent is any compatible volatile aprotic relatively polar solvent. Preferably, these materials have boiling points greater than about 80° C. to simplify manufacture and increase the shelf life of the electrolyte/battery. Typical examples of solvent are mixtures of such materials as propylene carbonate, ethylene carbonate, gamma-butyrolactone anhydrous tetrahydrofuran, glyme, di-glyme, tri-glyme, tetraglyme, dimethyl-sulfoxide, dioxolane, sulfolane and the like. A particularly preferred solvent is disclosed in U.S. patent application Ser. No. 07/918,438, filed Jul. 22, 1992, now U.S. Pat. No. 5,262,253 which application is incorporated herein by reference in its entirety.

In the practice of the present invention, the macroglycol is a urethane oligomer, H—Y—H (See Formula III), which encompasses polyester groups of the formula —($R^2OC(O)R^3C(O)O)_n$— and/or poly(oxyalkylene) units of the formula, —$(CH_2CHR^1O)_n$—, bonded together by a urethane linking group. The chemical linking reaction is carried out in an excess of glycol to assure that the macroglycol is hydroxyl group terminated.

The urethane oligomer macroglycol is produced by the reaction of poly(oxyalkylene) glycol or polyester with an diisocyanate. In a preferred embodiment, the isocyanate is represented by the formula $OCNR^4NCO$, where $R^4$ is a $C_1$–$C_{12}$ hydrocarbylene. Any suitable diisocyanate may be used, but typical isocyanates are hexamethylene diisocyanate, toluene 2,4- and 2,6-diisocyanate, naphthalene-1,5-diisocyanate, methylene-4,4'-di-phenyl diisocyanate and the like, well known to the art from their extensive use in polyurethane production.

The urethane oligomer, i.e., —Y— in Formula I, is represented by Formula III,

   III

Where $Z_n$ has been heretofore defined, and —D— is the urethane linking moiety —$C(O)NHR^4NHC(O)O$—, where $R^4$ has heretofore been defined, and q is an integer from 1 to 100, indicating at least one urethane bond (q=1), preferably q is an integer from 5 to about 10.

The term "vinyl sulfonate-derivatized" refers to a molecule containing the vinyl sulfonate group herein represented by V, in Formula I: $V_k$—Y—$R_{2-k}$. For purposes of the present invention, the preferred vinyl sulfonate-group has the chemical formula $CH_2=C(R^5)S(O_2)$—, wherein $R^s$ is preferably H or a $C_1$–$C_7$ alkyl. The preferred vinyl sulfonate-derivatized urethane-oligomer is represented by Formula I, $V_k$—Y—$R_{2-k}$, where V is the aforementioned sulfonate group, Y is the aforementioned urethane oligomer, and R is hydrogen or a $C_1$–$C_{20}$ hydrocarbyl group.

The vinyl sulfonate group is appended to the molecule to provide sites for crosslinking of the polymer precursor to other molecules in the electrolyte, thereby creating a solid polymeric matrix. k is the integer 1 or 2, representing mono-or di-sulfonated urethane oligomer.

The term "hydrocarbyl" and "hydrocarbylene" refer to monovalent and divalent organic radicals composed of carbon and hydrogen which may be aliphatic, alicyclic, aromatic or combinations thereof, e.g. aralkyl. Examples of hydrocarbylene groups include alkylene such as ethylene, propylene, and the like, arylene such as phenylene, naphthalene, and the like, hydrocarbyl groups include alkyl, such as methyl, ethyl, propyl, butyl, isobutyl, pentyl, hexyl, heptyl, octyl and the like, alkenyls such as propenyl, isobutenyl, hexenyl, octenyl and the like, aryl such as phenyl, alkylphenyl including 4-methylphenyl, 4-ethylphenyl and the like. Likewise, oxyhydrocarbyl refers to hydrocarbyl radicals containing minor amounts of unreactive oxygen, such as alkoxy, e.g. ethoxyethyl, propoxyethyl and the like.

The term "electrochemical cell" refers to a composite structure containing an anode, a cathode, and an ion-conducting electrolyte interposed therebetween.

The "anode" refers to an electrode for the half-cell reaction of oxidation on discharge which is typically comprised of a compatible anodic material. Such compatible anodic materials are well known in the art and include, by way of example, lithium, lithium alloys, such as alloys of lithium with aluminum, mercury, iron, zinc and the like, and intercalation based anodes such as carbon, tungsten oxides, intercalation-based anodes and the like.

The "cathode" refers to the counter-electrode to the anode and is typically comprised of a compatible cathodic material (i.e. insertion compounds) which is any material which functions as a cathode in an electrochemical cell. Such compatible cathodic materials are well known to the art and include, by way of example, manganese oxides, molybdenum oxides, vanadium oxides such as $V_6O_{13}$, lithiated cobalt oxides, lithiated nickel oxides sulfides of molybdenum, titanium and niobium, chromium oxides, copper oxides and the like. The particular compatible cathodic material employed is not critical.

Methodology

Methods for preparing the solid polymeric matrix and solid electrolyte are well known in the art. The present invention however, utilizes a particular polymer precursor in the preparation of the solid polymeric matrix. The polymer precursor is a vinyl sulfonate-derivatized macroglycol. The macroglycol is a urethane oligomer, i.e., the reaction product of dihydroxy-terminated compounds and a diisocyanate. Polyester or poly(oxyalkylene) are the dihydroxy-terminated compounds.

The preparation of the urethane oligomer is based on the reaction of a diisocyanate with excess dihydroxy-terminated polyester or poly(oxyalkyleneglycol). It is preferably prepared by reacting glycol and diisocyanate in molar ratio of from about 1:0.9 to about 1:0.1 under moderate temperature conditions, near ambient and usually no higher than 100° C. Significantly higher temperatures are avoided to prevent degradation. Reference is made to known methods in the art of polymer synthesis as disclosed in, for example, J. K. Backus et al., "Polyurethanes", in the "Encyclopedia of Polymer Science and Engineering", 13:243–303 (1988); C. E. Schildknecht (ed.), "Polymerization Processes", Wiley-Interscience, N.Y. ( 1977); J. H. Saunders et al., "Polyurethane: Chemistry and Technology", Wiley-Interscience, N.Y., Part I (1962), Part II, (1964); Phillips et al., "Polyurethanes, Chemistry, Technology and Properties", Gordon and Breach, N.Y. (1964); the disclosure of each of which is incorporated by reference in its entirety as if fully set forth herein in ipsis verbis.

It is within the scope of this invention to include a small proportion of diamine, such as ethylene diamine, in a step reaction, if the proportions of glycol and diisoeyanate are reversed in the initial step herein above. That is, if glycol is first reacted with excess diisocyanate, and the product is then reacted with diamine and diisocyanate in a second step, then a final step comprising the reaction of the product of the second step with diisocyanate and excess glycol results in a blockcopolymer of "hard segments" and "soft segments" as is well known in the art of polyurethane manufacturer referenced herein above.

The preparation of the vinyl sulfonate-derivatized polymer precursor, is based on the reaction of the macroglycol, with vinyl sulfonyl chloride. The hydroxy-terminated macroglycol reacts directly with the acid chloride under esterification conditions to produce the polymer precursor, as disclosed in U.S. application Ser. No. 07/918,438, filed Jul. 22, 1992, now U.S. Pat. No. 5,262,253 which is incorporated herein by reference in its entirety.

The manufacture of electrochemical cells and batteries is as disclosed for the polymer precursor of U.S. application Ser. No. 08/168,881, filed Dec. 15, 1993, the disclosure of which is incorporated herein by reference in its entirety.

What I claim is:

1. A solid electrolyte polymer precursor represented by Formula I:

$$V_k\text{—}Y\text{—}R_{2\text{-}k} \qquad \text{I.}$$

wherein k is 1 or 2;

R is H or $C_1$–$C_6$ alkyl; and

V represents Formula II:

$$CH_2=C(R^5)S(O_2)\text{—} \qquad \text{II.}$$

wherein Y represents Formula III:

$$\text{—}O(Z_nD)_qZ_n\text{—} \qquad \text{III.}$$

wherein $Z_n$ represents

—$(R^2OC(O)R^3C(O)O)_n$—;

D represents —C(O)NHR$^4$NHC(O)O—;

$R^1$ is H or $C_1$–$C_3$ alkyl;

$R^2$ is $C_1$–$C_{12}$ hydrocarbylene or oxyhydrocarbylene;

$R^3$ and $R^4$ are independently $C_1$–$C_{12}$ hydrocarbylene groups;

$R^5$ is H or $C_1$–$C_7$ hydrocarbyl;

n is an integer from 1 to about 50; and q is an integer from 1 to about 100.

2. A solid electrolyte comprising:

a solid polymer matrix;

a solvent; and an organic ion salt;

wherein said polymer matrix is obtained by curing the polymer precursor of claim 1.

3. A solid electrolyte according to claim 2 wherein said curing is accomplished by exposure to actinic radiation.

4. An electrochemical cell comprising:

an anode;

a cathode; and solid electrolyte of claim 2 interposed therebetween.

5. A solid electrolyte according to claim 2 wherein the polymer precursor has a number average molecular weight in the range of from about 4,000 to about 15,000.

6. An electrochemical cell according to claim 4 wherein the anode is an intercalation based anode comprising carbon.

7. An electrochemical cell according to claim 6 wherein the cathode comprises cathodic material selected from the group consisting of vanadium oxides and lithiated cobalt oxides.

8. A battery comprising at least two cells of claim 4.

9. A battery according to claim 8 wherein the anode is an intercalation based anode comprising carbon.

10. An electrochemical cell according to claim 4 wherein the polymer precursor has a number average molecular weight in the range of from about 4,000 to about 15,000.

11. A solid electrolyte polymer precursor according to claim 1, wherein the polymer precursor has a number average molecular weight in the range of from about 4,000 to about 15,000.

* * * * *